United States Patent [19]

McCarthy et al.

[11] Patent Number: 5,256,393
[45] Date of Patent: Oct. 26, 1993

[54] USE OF AZEOTROPIC DISTILLATION IN PROCESS TO DRY 5-AMINO-N,N'BIS (2,3-DIHYDROXYPROPYL)-2,4,6-TRIIODOISPHTHALAMIDE

[75] Inventors: William Z. McCarthy, St. Louis; Mills T. Kneller, University City; Youlin Lin, Chesterfield; David H. White, Florissant, all of Mo.

[73] Assignee: Mallinckrodt Medical, Inc., St. Louis, Mo.

[21] Appl. No.: 686,104

[22] Filed: Apr. 16, 1991

[51] Int. Cl.$^5$ ............... A61K 49/04; C07C 67/02; C07C 233/64
[52] U.S. Cl. .................... 424/5; 560/251; 564/153; 564/156
[58] Field of Search ............... 564/153, 156; 424/5; 560/251

[56] References Cited

U.S. PATENT DOCUMENTS 4,705,604 11/1987 Vanlautem et al. ............... 203/14

OTHER PUBLICATIONS

Organic Chemistry, Morrison and Boyde, 5th ed. p. 842 (1992).

*Primary Examiner*—José G. Dees
*Assistant Examiner*—Joseph M. Conrad
*Attorney, Agent, or Firm*—Rita Downard Vacca

[57] ABSTRACT

The use of azeotropic distillation to dry 5-amino-N,N'bis(2,3-dihydroxypropyl)-2,4,6-triiodoisophthalamide, an intermediate in the production of N,N'-bis(2,3-dihydroxypropyl)-5-N-(2-hydroxyethyl)glycolamido-2,4,6-triiodoisophthalamide.

26 Claims, No Drawings

USE OF AZEOTROPIC DISTILLATION IN PROCESS TO DRY 5-AMINO-N,N'BIS (2,3-DIHYDROXYPROPYL)-2,4,6-TRIIODOISPHTHALAMIDE

FIELD OF THE INVENTION

This invention relates to a process for the preparation of N,N'-bis(2,3-dihydroxypropyl)-5-N-(2-hydroxyethyl)glycolamido-2,4,6-triiodoisophthalamide, hereinafter called by its generic name, ioversol. More particularly, this invention relates to the use of azeotropic distillation to dry 5-Amino-N,N'-bis(2,3-dihydroxypropyl)-2,4,6-triiodoisophthalamide, an intermediate in the production of Ioversol, to eliminate the need for a forced air drying process.

BACKGROUND OF THE INVENTION

Ioversol was disclosed as a useful nonionic x-ray contrast agent in U.S. Pat. No. 4,396,598. An intermediate in the production of ioversol is 5-amino-N,N'-bis(2,3-diacetoxypropyl)-2,4,6-triiodoisophthalamide (tetraacetate) having the following structure:

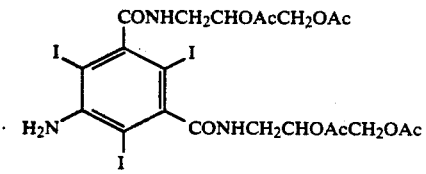

FORMULA 1

This compound and its use in producing ioversol are disclosed in U.S. Pat. No. 4,396,598 incorporated herein by reference. Tetraacetate, as disclosed therein, may be produced by acetylating a compound of the following structure:

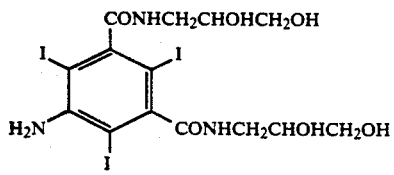

FORMULA 2

The acetylation is carried out by reacting 5-amino-N,N'-bis(2,3-dihydroxypropyl)-2,4,6-triiodoisophthalamide (tetrahydroxy) with acetic anhydride in N,N,-dimethylacetamide (DMAC) using 4-dimethylaminopyridine (DMAP) as a catalyst. The incorporated acetates in this reaction serve as blocking groups or agents to prevent any side reactions from occurring during the subsequent synthetic manipulations. Other blocking agents could also be used, such as, but not limited to dihydropyran, methoxymethylene acetal, ethoxymethylene acetal, acetate ester, chloroacetate ester, benzoate ester, benzylidine acetal, isopropylidine acetal, and cyclic carbonate. Upon completion of the reaction, the mixture is diluted with 1,1,2-trichloroethane and extracted with aqueous sodium carbonate solution to produce tetraacetate.

The resulting tetraacetate, in three additional synthetic steps is converted to ioversol, a compound of the following structure:

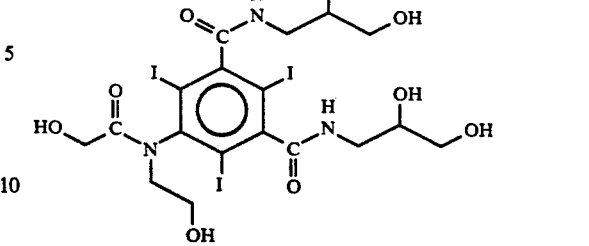

Formula 3

This procedure used to produce ioversol heretofore required a forced air drying process to remove water from the crystallized tetrahydroxy, which when prepared in the factory usually contains 20 to 30% water after having been centrifuged. The forced air drying process used in this process is slow and labor intensive.

An alternative method that would eliminate the need for the forced air drying process to remove water from the tetrahydroxy prior to use thereof was desired. It is an object of the present invention to meet this need.

SUMMARY OF THE INVENTION 5-amino-N,N'-bis(2,3-diacetoxypropyl)-2,4,6-triiodoisophthalamide (tetraacetate) is produced by acetylation of 5-amino-N,N'-bis(2,3-dihydroxypropyl)-2,4,6-triiodoisophthalamide (tetrahydroxy) with acetic anhydride with a catalyst, preferably N,N,-dimethylaminopyridine. Prior to the acetylation of the tetrahydroxy which, for all practical purposes is insoluble, i.e., approximately 1% solubility in water at 25° C., the non-isolated product is dried by azeotropic distillation with an organic solvent such as 1,1,2-trichloroethane, and then subsequently converted to tetraacetate in a one step operation.

This process has the advantages of not requiring the tetrahydroxy to be isolated or physically dried. Elimination of the drying procedure eliminates the capital cost of a dryer, improves attendant safety, and is faster, more economical, and less labor intensive.

DETAILED DESCRIPTION OF THE INVENTION 5-amino-N,N'-bis(2,3-diacetoxypropyl)-2,4,6-triiodoisophthalamide (tetraacetate) as disclosed in U.S. Pat. No. 4,396,598 discussed above, may be prepared generally by drying 5-amino-N,N'-bis(2,3-dihydroxypropyl)-2,4,6-triiodoisophthalamide(tetrahydroxy) containing 10 to 40% water, but more commonly 20 to 30% water, with an azeotropic solvent such as for example toluene, xylene, a halocarbon solvent or a chlorocarbon solvent. The tetrahydroxy must be sufficiently dried in order to effectuate the acetylation thereof with acetic anhydride. Successful and thorough azeotropic drying of tetrahydroxy which is, for all practical purposes, insoluble, i.e., approximately 1% solubility in water at 25° C., is unexpected since the hydroxyl groups of the tetrahydroxy bind water molecules very tightly. However, examples of azeotropic solvents effective in drying tetrahydroxy include but are not limited to carbon tetrachloride, dichloromethane, chloroform, 1,2-dichloroethane, 1,1,2-trichloroethylene, 1,1,2-trichloroethane, 1,1,1-trichloroethane and tetrachloroethylene, but most preferably 1,1,2-trichloroethane.

1,1,2-trichloroethane forms a low boiling azeotrope with water at 86° C. with a composition of 16 percent water by weight. The distillate can be monitored for water content by a Karl Fisher test. After the water level is sufficiently reduced, N,N-dimethylacetamide (DMAC) is added and the distillation continues to effect a solvent exchange. Tetrahydroxy is not very soluble in the azeotropic solvent, e.g. 1,1,2-trichloroethane, in the initial mixture, which is actually a slurry. However, the tetrahydroxy begins to dissolve as the distillation and solvent exchange progress. The final mixture contains dry tetrahydroxy dissolved in DMAC with some level of the azeotropic solvent present. This azeotropic drying process would likewise work on similar such compounds which show low water solubility characteristics such as described above for the tetrahydroxy compound. The dried tetrahydroxy is then acetylated with acetic anhydride in N,N,-dimethylacetamide using 4-dimethylaminopyridine as a catalyst. Upon completion of the reaction, the mixture is diluted with 1,1,2-trichloroethane or a like solvent and extracted with an aqueous sodium carbonate solution to remove the by-product, acetic acid and to produce tetraacetate as illustrated by the reaction below.

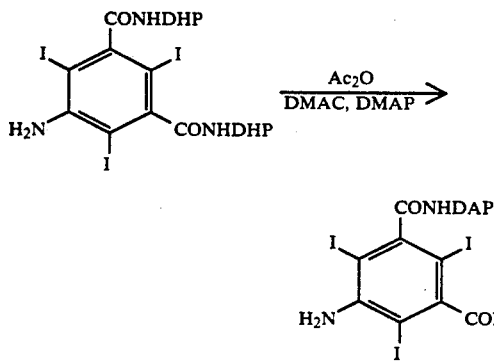

DMAC = N,N-dimethylacetamide
DMAP = 4-dimethylaminopyridine
DHP = CH$_2$CHOHCH$_2$OH
DAP = CH$_2$CHOACCH$_2$OAC The process of the present invention may be carried out according to the following specific example:

EXAMPLE 1

To 500 g of wet 5-amino-N,N'-bis(2,3-dihydroxypropyl)-2,4,6-triiodoisophthalamide was added 1.0 L 1,1,2-trichloroethane in a 3L three-neck round bottom flask using a mechanical stirrer. The flask was then heated to a temperature in the range of 40° to 90° C., the preferred range being 50° to 70° C. for 1 to 4 hours. A water aspirated vacuum was applied during the heating process. The 1,1,2-trichloroethane and water were then distilled. (NOTE: 5-amino-N,N'-bis(2,3-dihydroxypropyl)-2,4,6-triiodoisophthalamide did not dissolve.) After approximately 700 mL of 1,1,2-trichloroethane was added to the flask, distillation was continued. After approximately 200 mL of 1,1,2-trichloroethane and water was collected, 450 mL dimethylacetamide was added. Distillation continued until the density of the distillate was 0.95 to 0.96 gm/mL. Dimethylacetamide (200 mL) was then added to the contents of the flask and cooled to 55° C. 4-dimethylaminopyridine (3.75 g) DMAP was then added and 280 g acetic anhydride was added dropwise while monitoring the reaction by HPLC each hour following the addition thereof. 860 mL 1,1,2-trichloroethane was added (optionally 2% or 17 ml of amyl acetate may also be used in combination with the 1,1,2-trichloroethane) and the aqueous extractions were then begun. The first extraction using 20 g Na$_2$CO$_3$/1.58L water was stirred with the 1,1,2-trichloroethane layer for approximately ½ hour. The 1,1,2-trichloroethane layer was then drawn off. The pH was within the range of 7.8 to 8.1 by pH paper. The second extraction using 100 g NaCl/1 L water was likewise stirred with the 1,1,2-trichloroethane layer for ½ hour. The 1,1,2-trichloroethane layer was again drawn off.

After the aqueous extractions, distillation was used to remove approximately 70% of the 1,1,2-trichloroethane using a water bath to heat the solution and a water aspirator to produce the vacuum. 1,1,2-trichloroethane (600 mL) was collected off the 5-amino-N,N'-bis(2,3-diacetoxypropyl)-2,4,6-triiodoisophthalamide.

Pyridine may also be used as a catalyst in the above reaction although 4-dimethylaminopyridine (DMAP) is the catalyst of choice.

The dilution as described above may also be carried out using other organic solvents such as for example toluene, a halocarbon solvent or a chlorocarbon solvent. Examples of such solvents include but are not limited to carbon tetrachloride, dichloromethane, chloroform, 1,2-dichloroethane, 1,1,2-trichloroethylene, 1,1,2-trichloroethane, 1,1,1-trichloroethane and tetrachloroethylene, but most preferably 1,1,2-trichloroethane.

In addition to sodium carbonate, sodium chloride, sodium bicarbonate, ammonium hydroxide, potassium carbonate, or potassium bicarbonate may be used for the aqueous extractions above-described although sodium carbonate or potassium carbonate are the salts of preference for the first extraction.

As various changes could be made in the above process without departing from the scope of the invention, it is intended that all matter contained in the above description or shown in the above figures shall be interpreted as illustrative and not in a limiting sense.

Accordingly, having described our invention, we claim:

1. A process for the production of 5-amino-N,N'-bis(2,3-diacetoxypropyl)-2,4,6-triiodoisophthalamide from 5-amino-N,N'-bis(2,3-dihydroxypropyl)-2,4,6-triiodoisophthalamide comprising the steps of:
   a. drying the 5-amino-N,N'-bis(2,3-dihydroxypropyl)-2,4,6-triiodoisophthalamide by azeotropic distillation with a solvent,
   b. acetylating 5-amino-N,N'-bis(2,3-dihydroxypropyl)-2,4,6-triiodoisophthalamide with an acetylating agent in N,N,-dimethylacetamide and a catalyst to produce 5-amino-N,N'-bis(2,3-diacetoxypropyl)-2,4,6-triiodoisophthalamide,
   c. diluting said 5-amino-N,N'-bis(2,3-diacetoxypropyl)-2,4,6-triiodoisophthalamide with an organic solvent, and
   d. extracting by-product from said 5-amino-N,N'-bis(2,3-diacetoxypropyl)-2,4,6-triiodoisophthalamide with an aqueous solution.

2. The process of claim 1 wherein said solvent is selected from a group consisting of toluene, xylene, a halocarbon solvent, and a chlorocarbon solvent.

3. The process of claim 1 wherein said solvent is selected from a group consisting of carbon tetrachloride, dichloromethane, chloroform, 1,2-dichloroethane, 1,1,2-trichloroethylene, 1,1,2-trichloroethane, 1,1,1-trichloroethane and tetrachloroethylene.

4. The process of claim 1 wherein said solvent is 1,1,2-trichloroethane.

5. The process of claim 1 wherein said acetylating agent is acetic anhydride.

6. The process of claim 1 wherein said acetylating agent serves as a blocking agent.

7. The process of claim 1 wherein said catalyst is selected from the group consisting of 4-dimethylaminopyridine and pyridine.

8. The process of claim 1 wherein said catalyst is 4-dimethylaminopyridine.

9. The process of claim 1 wherein said organic solvent is selected from the group consisting of toluene, a halocarbon solvent and a chlorocarbon solvent.

10. The process of claim 1 wherein said organic solvent is selected from a group consisting of carbon tetrachloride, dichloromethane, chloroform, 1,2-dichloroethane, 1,1,2-trichloroethylene, 1,1,2-trichloroethane, 1,1,1-trichloroethane and tetrachloroethylene.

11. The process of claim 1 wherein said organic solvent is 1,1,2-trichloroethane.

12. The process of claim 1 wherein said aqueous solution is selected from the group consisting of sodium chloride, sodium carbonate, sodium bicarbonate, ammonium hydroxide, potassium carbonate and potassium bicarbonate.

13. The process of claim 1 wherein said aqueous solution is a sodium chloride solution.

14. A process for the production of 5-amino-N,N'-bis(2,3-diacetoxypropyl)-2,4,6-triiodoisophthalamide from 5-amino-N,N'-bis(2,3-dihydroxypropyl)-2,4,6-triiodoisophthalamide comprising the steps of:
 a. drying the 5-amino-N,N'-bis(2,3-dihydroxypropyl)-2,4,6-triiodoisophthalamide crystals by azeotropic distillation with a solvent,
 b. reacting 5-amino-N,N'-bis(2,3-dihydroxy-propyl)-2,4,6-triiodoisophthalamide with a blocking agent in N,N,-dimethylacetamide and a catalyst to produce 5-amino-N,N'-bis(2,3-diacetoxypropyl)-2,4,6-triiodoisophthalamide,
 c. diluting said 5-amino-N,N'-bis(2,3-diacetoxypropyl)-2,4,6-triiodoisophthalamide with an organic solvent, and
 d. extracting by-product from said 5-amino-N,N'-bis(2,3-diacetoxypropyl)-2,4,6-triiodoisophthalamide with an aqueous solution.

15. The process of claim 14 wherein said solvent is selected from a group consisting of toluene, xylene, a halocarbon solvent, and a chlorocarbon solvent.

16. The process of claim 14 wherein said solvent is selected from a group consisting of carbon tetrachloride, dichloromethane, chloroform, 1,2-dichloroethane, 1,1,2-trichloroethylene, 1,1,2-trichloroethane, 1,1,1-trichloroethane and tetrachloroethylene.

17. The process of claim 14 Wherein said solvent is 1,1,2-trichloroethane.

18. The process of claim 14 wherein said blocking agent is acetic anhydride.

19. The process of claim 14 wherein said blocking agent is selected from the group consisting of dihydroxypyran, methoxymethylene acetal, ethoxymethylene acetal, acetate ester, chloroacetate ester, benzoate ester, benzylidine acetal, isopropylidine acetal and cyclic carbonate.

20. The process of claim 14 wherein said catalyst is selected from the group consisting of 4-dimethylaminopyridine and pyridine.

21. The process of claim 14 wherein said catalyst is 4-dimethylaminopyridine.

22. The process of claim 14 wherein said organic solvent is selected from the group consisting of toluene, a halocarbon solvent and a chlorocarbon solvent.

23. The process of claim 14 wherein said organic solvent is selected from a group consisting of carbon tetrachloride, dichloromethane, chloroform, 1,2-dichlorothane, 1,1,2-trichloroethylene, 1,1,2-trichloroethane, 1,1,1-trichloroethane and tetrachloroethylene.

24. The process of claim 14 wherein said organic solvent is 1,1,2-trichloroethane.

25. The process of claim 14 wherein said aqueous solution is selected from the group consisting of sodium chloride, sodium carbonate, sodium bicarbonate, ammonium hydroxide, potassium carbonate and potassium bicarbonate.

26. The process of claim 14 wherein said aqueous solution is a sodium carbonate solution.

* * * * *